United States Patent
Fisher et al.

(10) Patent No.: US 9,211,153 B2
(45) Date of Patent: Dec. 15, 2015

(54) EXPANSION SCREW BONE TAMP

(75) Inventors: Michael A. Fisher, Lawrenceville, GA (US); Richard Techiera, Raynham, MA (US); Douglas Hester, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 507 days.

(21) Appl. No.: 12/984,486

(22) Filed: Jan. 4, 2011

(65) Prior Publication Data

US 2012/0172934 A1    Jul. 5, 2012

(51) Int. Cl.
| | |
|---|---|
| *A61B 17/04* | (2006.01) |
| *A61B 17/86* | (2006.01) |
| *A61F 2/08* | (2006.01) |
| *A61B 17/88* | (2006.01) |
| *A61B 17/84* | (2006.01) |

(52) U.S. Cl.
CPC .......... *A61B 17/8858* (2013.01); *A61B 17/844* (2013.01); *A61B 17/864* (2013.01); *A61B 17/8685* (2013.01); *A61B 17/8841* (2013.01)

(58) Field of Classification Search
CPC ............. A61B 17/844; A61B 17/8685; A61B 17/864; A61B 17/8858
USPC ........... 606/300–331; 411/325, 271, 383–385
See application file for complete search history.

(56) References Cited

U.S. PATENT DOCUMENTS

| | | | |
|---|---|---|---|
| 2,381,050 A | 8/1945 | Hardinge | |
| 2,954,718 A * | 10/1960 | Brilmyer | 411/70 |
| 4,091,806 A | 5/1978 | Aginsky | |
| 4,760,843 A | 8/1988 | Fischer | |
| RE33,348 E | 9/1990 | Lower | |
| 5,084,050 A | 1/1992 | Draenert | |
| 5,108,404 A | 4/1992 | Scholten | |
| 5,209,753 A * | 5/1993 | Biedermann et al. | 606/304 |
| 5,489,210 A | 2/1996 | Hanosh | |
| 5,704,936 A | 1/1998 | Mazel | |
| 5,713,903 A * | 2/1998 | Sander et al. | 606/326 |
| 5,720,753 A | 2/1998 | Sander | |
| 5,725,581 A | 3/1998 | Brånemark | |
| 5,735,898 A | 4/1998 | Brånemark | |
| 6,168,597 B1 | 1/2001 | Biedermann | |
| 6,436,142 B1 | 8/2002 | Paes | |

(Continued)

FOREIGN PATENT DOCUMENTS

| | | |
|---|---|---|
| EP | 340413 | 11/1989 |
| EP | 567423 | 2/1997 |

OTHER PUBLICATIONS

Cook, Biomechanical Evaluation and Preliminary Clinical Experience With Expansive Pedicle Screw Design, *J Spinal Disorders*, vol. 13(3), Jun. 2000, pp. 230-236—abstract.

(Continued)

*Primary Examiner* — Kevin T Truong
*Assistant Examiner* — Si Ming Ku

(57) ABSTRACT

A method of compacting and stabilizing bone in the spine using an expandable screw and bone filler. The method includes placing an expanding screw through a pedicle and into a fractured vertebral body using established techniques; and expanding the screw within the body to create a cavity by tamping bone around the expanded aspect of the screw. The screw can be expanded and rotated about its rotational-axis to tamp bone adjacent to the expanded screw. After compaction, the screw is removed and the cavity is filled with bone filler.

10 Claims, 22 Drawing Sheets

(56) References Cited

U.S. PATENT DOCUMENTS

| | | | |
|---|---|---|---|
| 6,579,290 | B1 | 6/2003 | Hardcastle |
| 6,668,688 | B2 * | 12/2003 | Zhao et al. .................. 81/439 |
| 6,767,350 | B1 | 7/2004 | Lob |
| 7,235,079 | B2 | 6/2007 | Jensen |
| 7,857,840 | B2 * | 12/2010 | Krebs et al. ................ 606/327 |
| 2002/0049447 | A1 | 4/2002 | Li |
| 2006/0106390 | A1 | 5/2006 | Jensen |
| 2007/0233249 | A1 | 10/2007 | Shadduck |
| 2007/0233250 | A1 | 10/2007 | Shadduck |
| 2008/0288003 | A1 * | 11/2008 | McKinley .................. 606/313 |
| 2009/0138043 | A1 * | 5/2009 | Kohm ........................ 606/246 |
| 2009/0264941 | A1 | 10/2009 | Banouskou |
| 2009/0281580 | A1 * | 11/2009 | Emannuel .................. 606/304 |
| 2010/0174289 | A1 * | 7/2010 | Schaller ....................... 606/99 |
| 2011/0046682 | A1 * | 2/2011 | Stephan et al. ............. 606/305 |

OTHER PUBLICATIONS

Frankel, Segmental Polymethylmethacrylate-augmented Pedicle Screw Fixation in Patients with Bone Softening Caused by Osteoporosis and Metastatic Tumor Involvement: a Clinical Evaluation, *Neurosurgery*, vol. 61(3), Sep. 2007, pp. 531-539—abstract.

Jensen, Percutaneous Polymethylmethacrylate Vertebroplasty in the Treatment of Osteoporotic Vertebral Body Compression Fractures: Technical Aspects, *AJNR*, vol. 18, Nov. 1997, pp. 1897-1904.

\* cited by examiner

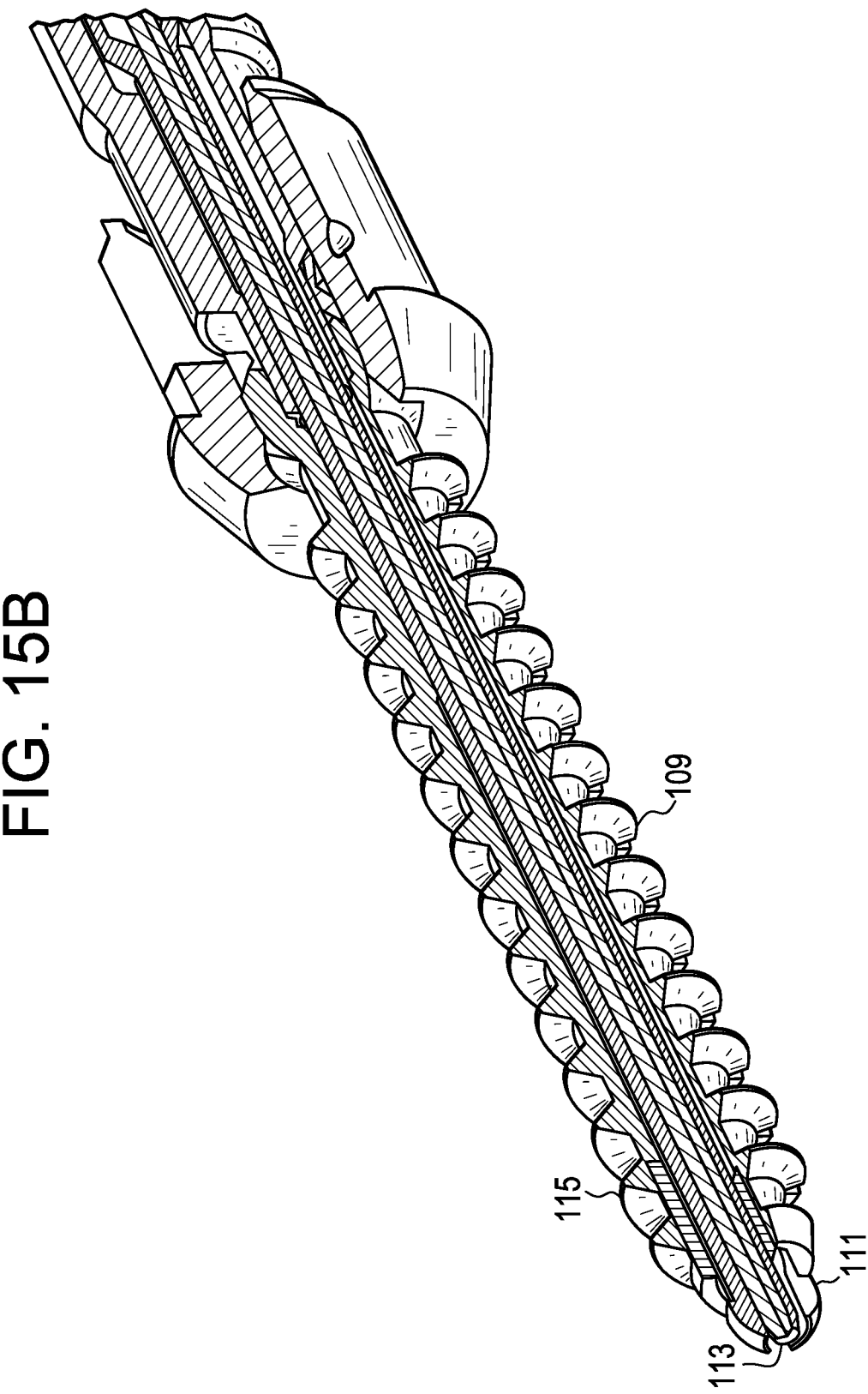

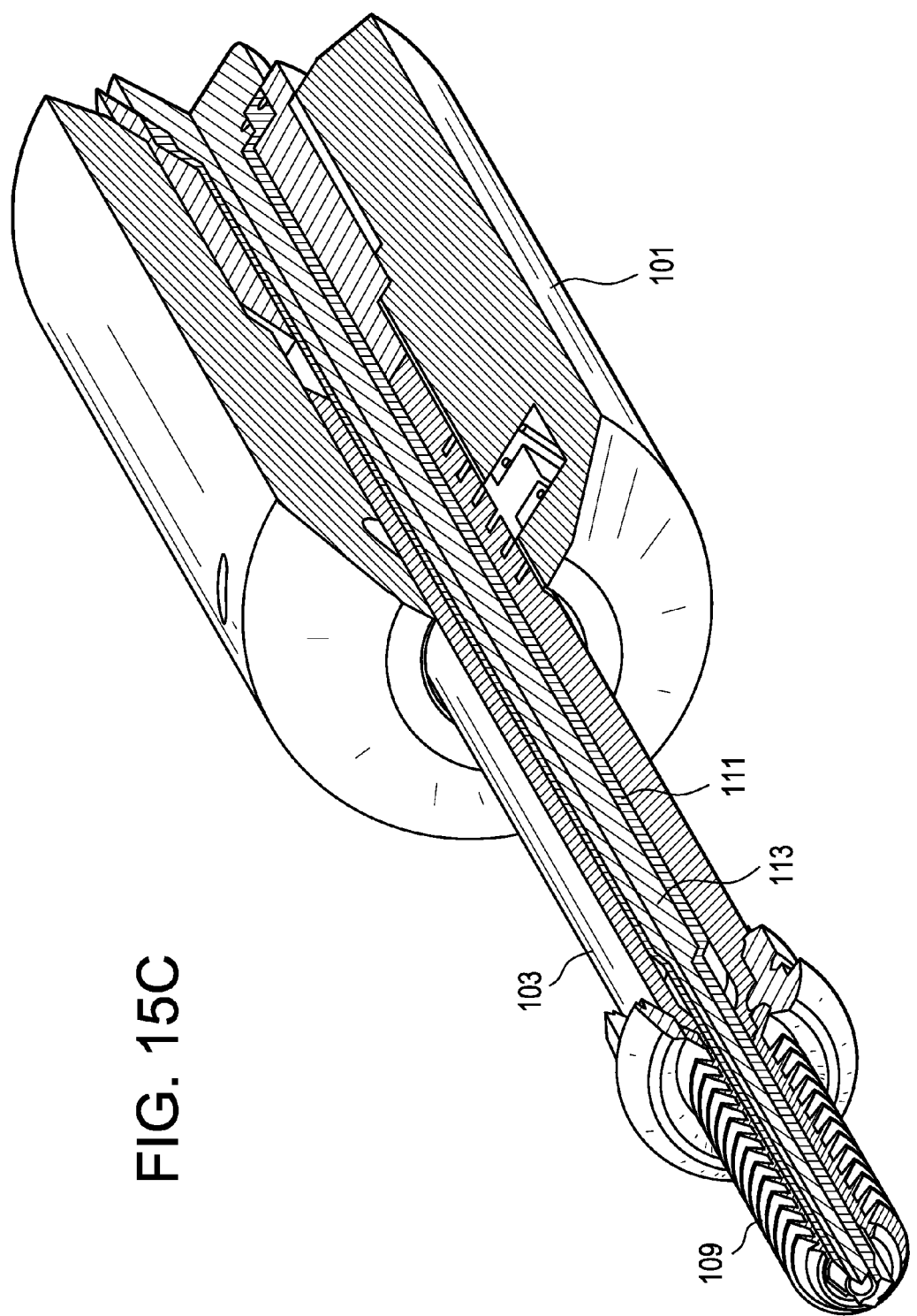

EXPANSION SCREW BONE TAMP

BACKGROUND OF THE INVENTION

In vertebroplasty, the surgeon seeks to treat a compression fracture of a vertebral body by injecting bone cement such as polymethylmethacrylate (PMMA) into the fracture site. In one clinical report, investigators describe mixing two PMMA precursor components (one powder and one liquid) in a dish to produce a viscous acrylic bone cement; filling 10 ml syringes with this cement, injecting it into smaller 1 ml syringes, and finally delivering the mixture into the desired area of the vertebral body through needles attached to the smaller syringes. Jensen *AJNR:* 18 Nov. 1997, Kyphoplasty is a method of practicing vertebral body augmentation in which a space is created in the fractured vertebral body in order to receive a bulking agent. The creation of such a space enhances the safety of the procedure, as the cement may be injected under low pressures. The cavity also creates a region of least resistance to cement flow, thereby lowering the risk of cement extravasation. Preferably, this space-creating technology may also restore at least a portion of any lost height in the vertebral body. In one such kyphoplasty technique, U.S. Pat. No. 5,108,404 ("Scholten") discloses inserting an inflatable device such as a balloon within a passage within the vertebral body, inflating the balloon to compact the surrounding cancellous bone and create an enlarged void in the vertebral body, and finally injecting bone cement into the void.

There is a desire to develop technologies that can create a space in a fractured vertebral body without using a balloon in order to deliver cement into the space in the vertebral body.

Expandable screws enjoy a positive clinical history and are indicated for use in spinal surgery. Expansion screws have clinical familiarity and are known in the practice of spinal medicine. Expanding pedicle screws have been used to compact trabecular bone within screw threads in an attempt to prevent screw pull-out or mechanical failure in osteoporotic patients with good results. Cook, *J Spinal Disorders* 13(3) 230-36, 2000. Similarly, cementation of pedicle screws in osteoporotic bone has been investigated with good results. Frankel, *Neurosurgery,* 61(3) 531-9, 2007.

Numerous patents and patent applications disclose the use of expandable screws for reducing fractured bones. See, for example, U.S. Pat. No. 2,381,050; U.S. Pat. No. 4,091,806; U.S. Pat. No. 4,760,843; and U.S. Pat. No. 5,209,753; U.S. Pat. No. 6,436,142; U.S. Pat. No. 5,704,936; US Patent Publication No. US2007-0233250; US Patent Publication No. US2007-0233249; and US Patent Publication No. US2009-0264941.

SUMMARY OF THE INVENTION

The present invention relates to a method of compacting and stabilizing fractured bone in the spine using an expandable sleeve and bone filler. In one preferred embodiment, the method comprises placing an expandable sleeve (such as a cannulated screw having a longitudinally slit shaft) through a pedicle and into a fractured vertebral body using conventional techniques; and expanding the sleeve within the body to thereby tamp bone around the expanded aspect of the sleeve. After tamping creates the desired level of compaction, the sleeve is collapsed and removed, and the resultant cavity is then filled with bone filler (such as a cement). Alternatively, the sleeve can remain in place and the bone filler can be placed through, in, or around the sleeve.

In preferred embodiments, the present invention involves the insertion and expansion of an expandable pedicle screw into a fractured vertebral body to tamp the trabecular bone surrounding the screw, collapsing and removing the screw to create a cavity in the vertebral body, followed by cement injection into the cavity so created.

Thus, the present invention contemplates the use of expansion screws as kyphoplasty-like cavity-creation devices.

In some embodiments, the expanded screw can be rotated about its longitudinal axis (as one normally turns a screw) to further tamp bone adjacent to the expanded screw.

In some embodiments, screw design features are optimized for cavity-creation rather than thread engagement. In some embodiments, screw design is optimized for deformation and bone compaction rather than for long-term load bearing. In some embodiments, the screw material of construction is optimized for maximal deflection and removal (i.e., no plastic deformation or adhesion to injected bone filler). In some embodiments, the screw geometry is optimized for radial deflections rather than axial pull-out or cantilever beam loading.

In some embodiments, the screw is used as a platform for needle placement and/or off-axis cement delivery, and so functions as a curved needle.

Therefore, in accordance with the present invention, there is provided a method of augmenting a fractured vertebral body in a patient, comprising the steps of:

a) selecting an expandable sleeve characterized by a collapsed configuration and an expanded configuration, and comprising a cannulated shaft having a bore, a proximal end, a distal end, and a plurality of longitudinal slits opening onto the distal end and forming at least two legs in the cannulated shaft, b) inserting the expandable sleeve into the fractured vertebral body in its collapsed configuration, c) expanding the sleeve to its expanded configuration to tamp the fractured vertebral body, d) returning the expanded sleeve to its collapsed configuration, e) removing the sleeve from the vertebral body to leave a cavity in the fractured vertebral body, and f) filling the cavity with bone cement.

DESCRIPTION OF THE DRAWINGS

FIGS. 15a-15c, disclose another instrument for creating a space in a vertebral body.

DETAILED DESCRIPTION OF THE INVENTION

Figure 1A:
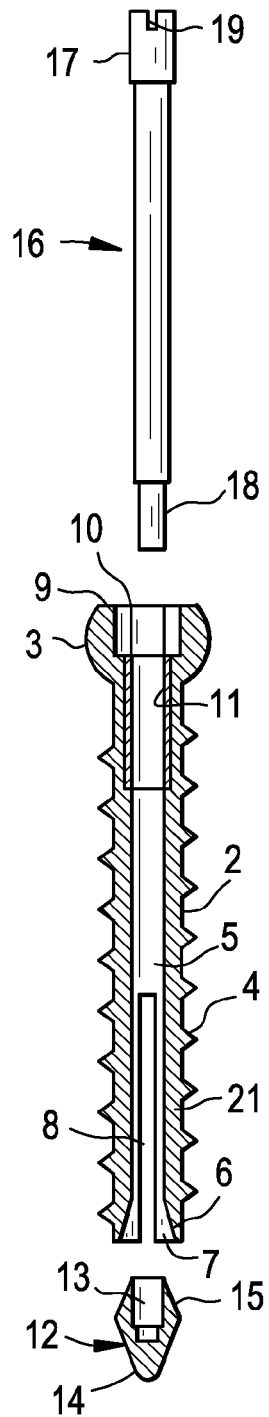
FIG. 1a discloses an exploded view of the bone screw, partially as sectional view.

The screw is a preferred embodiment of the expandable sleeve in the present invention because the threads thereon desirably control both insertion forces and axial motion.

In some embodiments, the expandable screw of the present invention can be substantially similar to that described in U.S. Pat. No. 5,209,753 (Biedermann), the specification of which is incorporated by reference in its entirety. Thus, some screws of the present invention are characterized by:
  a) an elongated shaft having a distal portion, an external thread and a proximal head, a longitudinal bore extending along the longitudinal axis of the shaft, an internal thread being provided in the longitudinal bore, a distal end of the bore having a tapered portion, and the shaft also having slits extending parallel to the longitudinal direction of the shaft to form a plurality of legs,
  b) a second shaft insertable into the longitudinal bore and having a threaded portion cooperating with the internal thread in the bore,
  c) an expander part (or "mandrel") received in the distal portion of the shaft and being larger in size than the longitudinal bore,
wherein the expander part and the second shaft are inserted into the longitudinal bore as a unit, with the expander part being a distal portion of the unit and the second shaft being the proximal portion of the unit.

In some embodiments, the expander part and the shaft are connected by a thread means, with the expander part being axially movable within the longitudinal bore as the second shaft is rotated.

In some embodiments, the expandable screw of the present invention can be substantially similar to one custom device manufactured for Dr. Kostuik's clinical use circa 2001.

In some embodiments, the expandable screw of the present invention can be substantially similar to the one described by U.S. Pat. No. 2,381,050 (Hardinge), the specification of which is incorporated by reference in its entirety. Thus, some screws of the present invention are characterized by a body member adapted to be inserted into a bore formed in the vertebral body, comprising:
  a) an elongated cylindrical member having its inner end laterally expandable to engage the walls of the bone bore and having its exterior surface at the inner end provided with screw threads,
  b) means extending through the body member and adapted to be accessible from the exterior of the distal bone for expanding the inner end into an anchored relation in the proximal bone,
  c) a nut member comprising a sleeve extending along and threaded upon the body member and having a head at its outer end adapted to bear against the exterior of the distal bone for drawings the anchored proximal bone into abutment with the distal bone, and
  d) means interengaging the body member and the nut member when the nut member in unscrewed a predetermined distance along the body member to prevent further unscrewing of the nut member, whereby further turning of the nut member will unscrew the members from the bone as a unit.

As shown in Table 1 below, it appears that the cavity volume created by expansion screw technology is substantially comparable to the cavity volume created by conventional balloon-based bone tamping technology:

TABLE 1

Volume of the Kyph-X ™ balloon tamp (15 mm diameter by 20 mm length)
Volume = Volume$_{sphere}$ + Volume$_{cylinder}$ = $\frac{4}{3} \pi R^3$ + L $\pi R^2$
Where: R = 15/2 mm and L = (20-15) mm = 5 mm
Volume = 2,650 mm$^3$
Volume of the Expandable Screw tamp (5 mm diameter, 25 mm length, 6 mm end split)
Volume = Volume$_{cylinder}$ + Volume$_{wedge}$ = L $\pi R^2$ + ½ L (2R) S
Where: R = 5/2 mm, L = 25 mm, and S = 6 mm
Volume = 870 mm$^3$
Volume of a Rotated Expandable Screw (5 mm diameter, 25 mm length, 6 mm end split)
Volume = Volume$_{truncated\ cone}$ = $\frac{1}{3} \pi (R_1^2 + R_1 R_2 + R_2^2)$ L
Where: R$_1$ = 5/2 mm, R2 = (5 + 6)/2 mm = 5.5 mm, and L = 25 mm
Volume = 1,320 mm$^3$ Thus, it appears that the volume of the cavity created by rotating a screw of the present invention can approach about half that of a conventional balloon used in vertebral body augmentation.

Several expansion mechanisms for expanding the sleeve of the present invention are contemplated as within the scope of the present invention. In some embodiments, a cannulated pedicle screw is distally cut along the length of its cannulated shaft to enable distal flanges of material (or legs) to deflect outwards as a mandrel is inserted proximally through the distal portion of the cannulation. In the Biedermann screw, the mandrel is proximally pulled into the distal portion of the shaft and the shaft is cut longitudinally into two 180° arced sections that deflect outwards. In some embodiments of the present invention, additional longitudinal cuts in the cannulated shaft are made so as to enable screw shaft deflections in more than two directions.

An expanded screw can be rotated about its axis to increase the amount of bone being tamped. Rotating an expanded screw about its longitudinal axis to further tamp local bone suggests the screw threads will continue to drive longitudinal motion as the rotation takes place. This rotating expanded screw may be more preferably embodied by using a threaded bushing 200 (shown in FIG. 15A) that enables rotation of one portion of the screw shank without requiring rotation at another portion of the screw shank. Creating a segment of screw threads that can engage with pedicular bone but are not required to rotate when the expanded screw is rotated would avoid any longitudinal movement. The distal (expanded) part of the screw might not require any or only minimal screw threads. The threads at the distal screw shank are preferably designed to enable post-expansion screw removal (especially if any plastic deformation has taken place due to the expansion mechanism).

The shape of the expanded screw can be controlled by placement of the deforming mandrel. Because local trabecular bone will resist the radial displacement of the screw shank, complex beam loading is expected. This mechanical loading can be used to shape the tamped space. A flexible beam with multiple expansion mandrels can assume a complex shape (similar to a stent). It may be desirable to expand a screw into a complex shape. Thus, mechanisms can be contemplated to enable multiple expansion mandrels. Similarly, screw shank sections can have varying mechanical properties (like varying beam strength, buckled beam shapes, material properties, etc.). Mechanical features may be included in the deflected screw shank sections that regulate the amount or shape of shank deflections. These mechanical features could also interface with the expansion mandrel (like hooks or lips that restrain radial deflections, enable controlled buckling, or enable rotational deflections during deployment). The deflecting screw shanks could be designed to deform or deflect laterally as they deflect radially. Such a design could be used to create a larger surface area during deflection—thus creating a larger cavity or spreading load. Alternatively, the screw shank can be configured in concentric layers that deflect in designed directions. This concentricity would produce a multi-directional net deflection (i.e. a split shank deflects in two directions and two split, nested shanks deflects in four directions).

In another alternative embodiment, a structural mesh surrounds the screw. Upon expansion, the screw deflects the mesh material outwardly. The deflecting mesh material tamps bone during this outward deflection. Such an embodiment increases the effective screw tamp surface area to include both the deflected shaft and the area between the shaft segments.

In some embodiments having a plurality of legs, there is provided a first leg having an elasticity, a second leg having an elasticity, and the elasticity of the first leg is greater than the elasticity of the second leg.

Once the expanded screw has tamped the bone surrounding it, the expanded screw may be re-collapsed and then removed from the vertebral body, thereby leaving behind a cavity suitable for filling by cement injection therein.

In some embodiments, collapse and removal of the expanded screw may be effected by moving the mandrel of the expanded screw distally (so that the mandrel no longer is in contact with the legs) and then pulling the sleeve proximally. The splayed legs of the sleeve will collapse as they are pulled into the cannula, thereby allowing for easy removal of the device.

In some embodiments, collapse and removal of the expanded screw may be helped by constructing at least the leg portion of the shaft from a shape memory metal, wherein the legs have a substantially linear memorized shape. In these embodiments, the surgeon may expand the sleeve as above to produce a sleeve having splayed legs. When the surgeon is ready to collapse the splayed legs, the surgeon moves the mandrel of the expanded screw distally (so that the mandrel no longer is in contact with the legs). With the distorting force of the mandrel removed, the legs revert to their linear memorized configuration. The sleeve is now in its collapsed configuration and can be easily pulled into the cannula, thereby allowing for easy removal of the device.

Therefore, in accordance with the present invention, there is provided a bone tamp comprising:
 a) an elongated shaft having a distal portion, an external thread and a proximal head, a longitudinal bore extending along the longitudinal axis of the shaft, an internal thread being provided in the bore, a distal portion of the bore being provided with a tapered recessed portion, and the shaft also having a plurality of slits extending parallel to the longitudinal direction of the shaft to produce a plurality of shaft legs,
 b) a second shaft inserted into the longitudinal bore and having a threaded surface cooperating with the internal thread in the bore,
 c) a mandrel received in the distal portion of the bore and being larger in size than the bore,
wherein the mandrel and the second shaft are inserted into the longitudinal bore as a unit, with the mandrel being a distal portion of the unit and the second shaft being the proximal portion of the unit,
whereby proximal movement of the mandrel into the bore splays the shaft legs from the elongated shaft at different angles,
wherein at least the plurality of shaft legs comprise a shape memory metal and are characterized by a linear memorized shape.

However, in other embodiments, once the expanded screw has tamped the bone surrounding it, the expanded screw may be left in place and cement may be injected around it.

In some preferred embodiments, the CONFIDENCE™ system, marketed by DePuy Spine, Inc., of Raynham, Mass., is used to inject cement into the cavity formed in the vertebral body. However, because the screw of the present invention may be cannulated, it may be possible to insert a traditional cement injection needle through the cannulated screw to inject cement into the formed cavity. Alternatively, a flexible needle could be deployed through the screw to inject cement to the periphery of the formed cavity or to create "off-axis" cavities. The injectate could be cement or infiltrated materials that improve bone growth or minimize chemical pain generators.

In some embodiments, the injectate could include a vasoconstrictor (such as epinephrine) to prevent cement embolization and fat emboli, and to minimize local bleeding post-operatively.

Figure 1B:
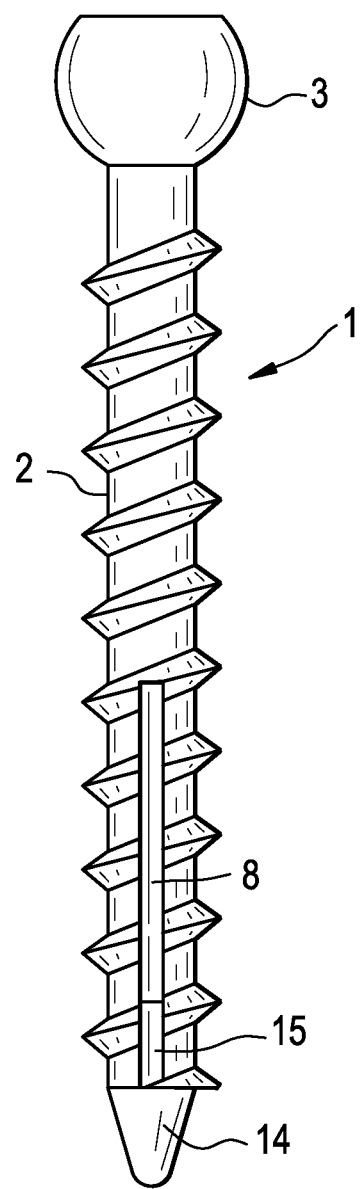
FIG. 1b discloses the assembled screw of FIG. 1a inserted into a fractured vertebral body in its collapsed configuration.
Figure 2:
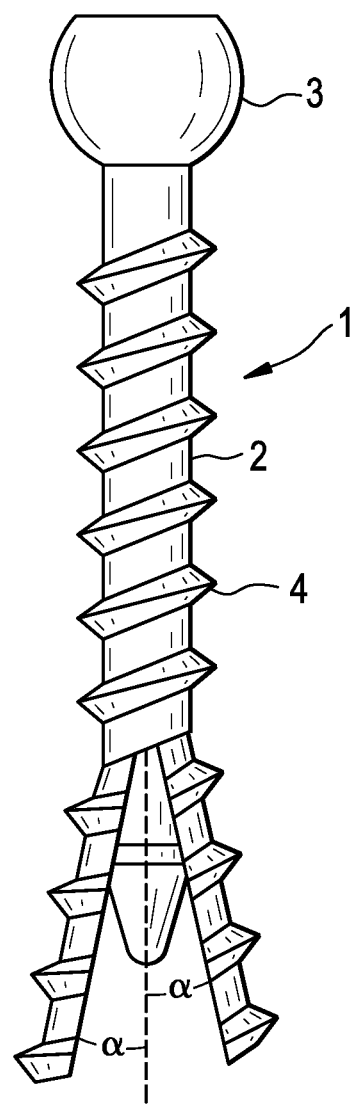
FIG. 2 discloses an expanded screw.

Referring now to FIGS. 1a-b and 2, there is provided an expandable screw of the present invention in its collapsed configuration, the screw comprising;
 a) a cannulated shaft having a bore, a proximal end portion having a head, a threaded distal end portion having a distal end, and a plurality of longitudinal slits opening onto the distal end and forming at least two legs in the cannulated shaft, each leg having an inner surface,
 b) a mandrel comprising a shaft and an enlarged distal end portion, the enlarged distal end portion having a proximal portion having a taper,
wherein the shaft of the mandrel is received in the bore, and wherein the enlarged distal end of the mandrel has a diameter greater than the bore and is located distal to the bore.

The bone screw 1 comprises a threaded shaft portion 2 formed unitary with a proximal head 3. The threaded shaft portion is provided with an external thread 4 as commonly used with bone screws. As can be seen from FIG. 1, a coaxially aligned longitudinal bore 5 extends through the interior of the screw. At the distal end 6 of the shaft opposite to the head, a tapered conical portion 7 is provided. Slits 8 extend parallel to the longitudinal direction of said threaded portion, forming legs 21. The axial length of the slits is at least equal to twice the length of the conical portion. Preferably, one pair of slits is provided, the slits being displaced by 180 degrees with respect to each other.

Opposite to the distal free end, the proximal head 3 is provided with a plane face arranged perpendicular with respect to the axis of symmetry. A recess 10 extends in axial direction which is formed to allow the screw to be screwed into a bone by a screw driver. The diameter of said recess is larger than the diameter of said longitudinal bore. Adjacent to the recess 10, a threaded portion 11 is arranged. Preferably, the length of this portion is at least twice the length of the tapered portion 7.

As can be seen from FIG. 1, the distal end of the bone screw is formed as a separate tip, or mandrel, 12. A coaxially aligned bore 13 is provided at the proximal end thereof, pointing towards the head. The distal end thereof has a point 14 corresponding to the tip of the bone screw. Opposite the tip, the proximal portion 15 of the mandrel has a conical shape tapering towards the conical portion 7 and formed to fit into the recessed portion 7.

A second shaft 16 is provided having a threaded proximal portion 17. The diameter and the pitch of this thread correspond to the interior thread of the portion 11 so that both threads may be joined. The diameter of the rest of the shaft 16 is dimensioned so it may be inserted into the longitudinal bore. Opposite to the threaded proximal portion 17, a second distal threaded portion 18 is provided which cooperates with an interior portion 18 and the pitch of the thread in the bore 13 are opposite to the pitch of the proximal threaded portion 17 and to the pitch of the corresponding interior thread in portion 11.

The length of the shaft 16 is selected such that the proximal threaded portion 18 extends into the tapered recessed portion 7 and the mandrel 12 can be screwed onto this portion. Consequently, as shown in FIG. 2, the mandrel 12 forms the normal point of the bone screw when the proximal threaded portion 17 of the second shaft is screwed to the end or at least close to the end of the threaded portion 11. A slit 19 is provided at the end of the proximal threaded portion into which a screw driver may be inserted.

In operation, the second shaft 16 is screwed into the longitudinal bore 5 to the end of the threaded portion 11. Next, the mandrel 12 is screwed onto the distal threaded portion 18 projecting into the tapered portion 7, thus forming the normal point of the screw, as shown in FIG. 2. If required, the head of the bone screw may be provided with a connecting part 20 which is movable with respect to said screw head, as described in DE 37 11 013 C. The connecting part serves to connect the screw with rods for the fixation of bone fragments, in particular spinal elements.

When the bone screw has been screwed into a bone, the second shaft 16 can be unscrewed into the direction of the proximal head 3 by inserting a screw driver into slit 19. Due to the opposite pitch of the threaded portions 17 and 18, the connection between the distal threaded portion 18 and the mandrel is maintained, the mandrel being pulled into the portion provided with slits, thus effecting an expansion of the threaded portion 2. Since the region in which force is transferred from the expander part to the threaded shaft is not deformed, a very precise adjustment is possible.

In a further embodiment, portion 11 may be provided with a greater diameter as compared to the diameter of the longitudinal bore 5, the diameter of the first threaded portion 17 having corresponding size.

According to a further example, the portion 11 has a smaller diameter than the adjacent portion of the longitudinal bore 5. The diameter of the first threaded portion corresponds to the interior thread of the portion 11. Shaft 16 and expander part 12 are formed unitary, the shaft 16 and the expander part being inserted from the free end 6 into the threaded portion 2. In this case, the first threaded portion 17 has a length such that the shaft may be moved—from a position in which the point 14 is positioned as shown in FIG. 2—toward the head, the expansion being effected by pulling the expander part into the slit portion.

In some embodiments, shaft 16 is cannulated, and bore 13 extends completely through mandrel 12, so as to provide a means of providing cement through the same instrument.

Referring now to FIG. 2, there is provided an expandable screw of the present invention in its expanded configuration. In this expanded configuration, the mandrel has moved proximally so that the proximal taper of its enlarged distal end portion bears against the respective inner surfaces of the legs, thereby expanding the legs.

Figure 3A:
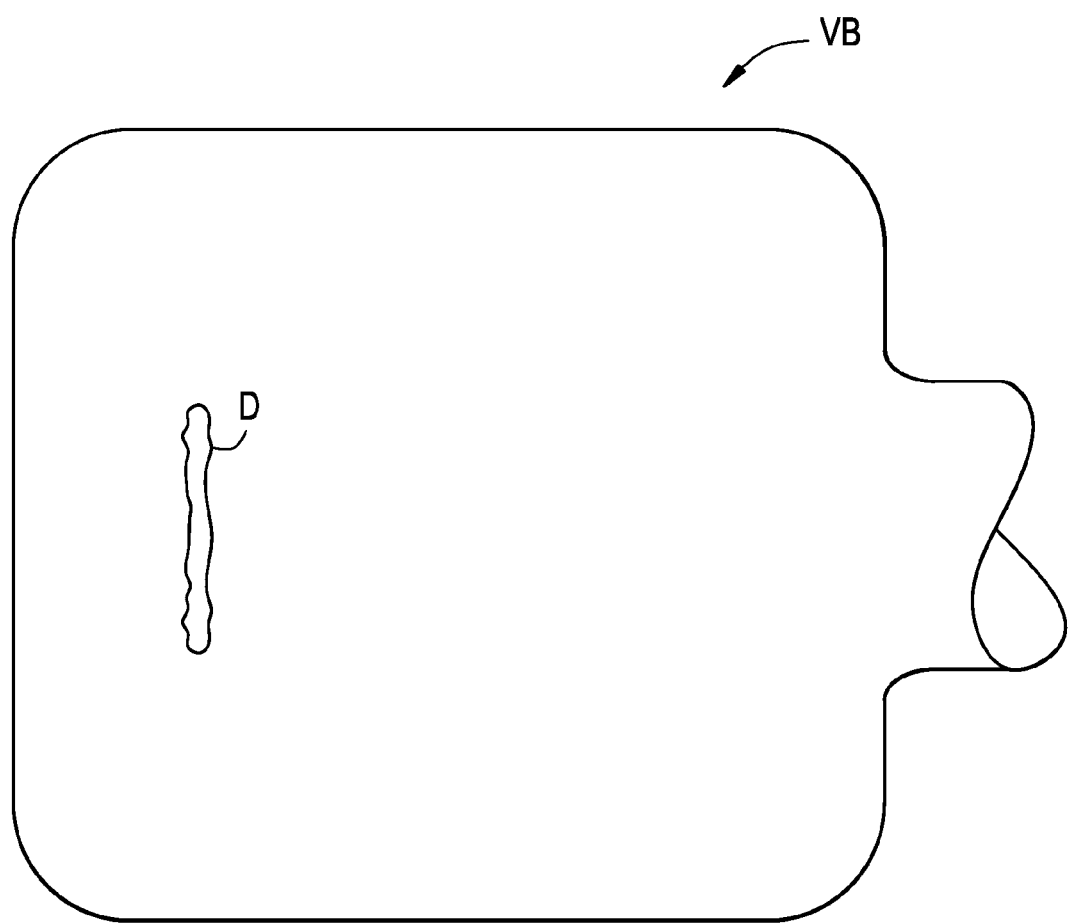
FIGS. 3a-3f disclose one preferred technique of practicing the present invention.
Figure 3B:
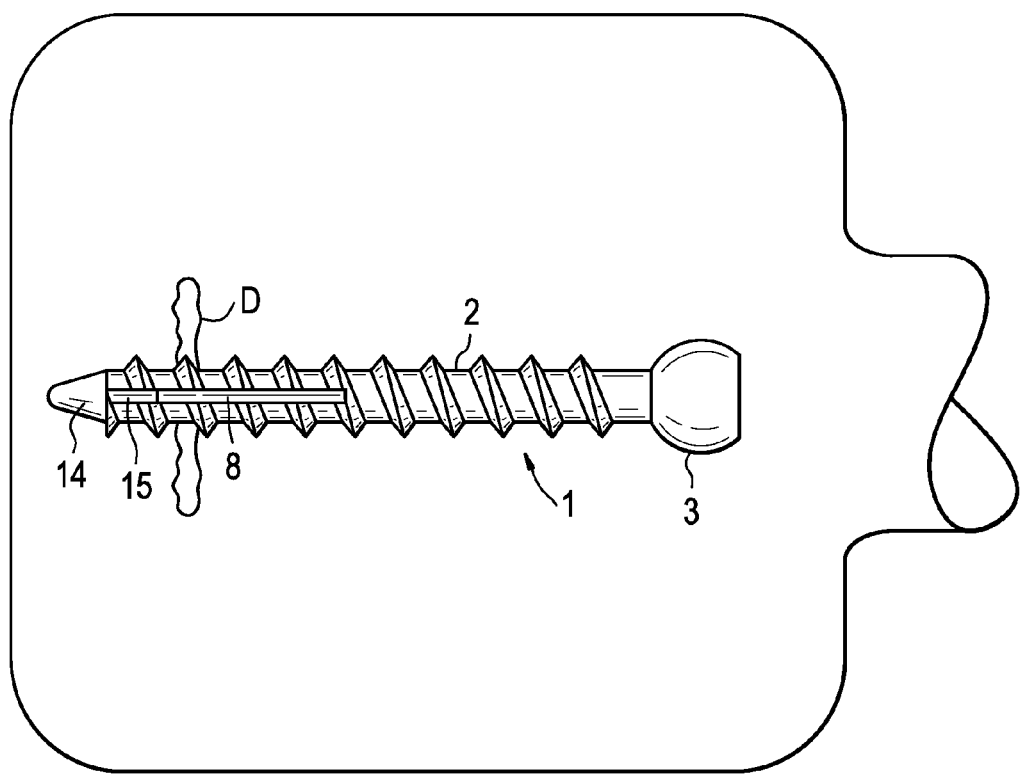
Figure 3C:
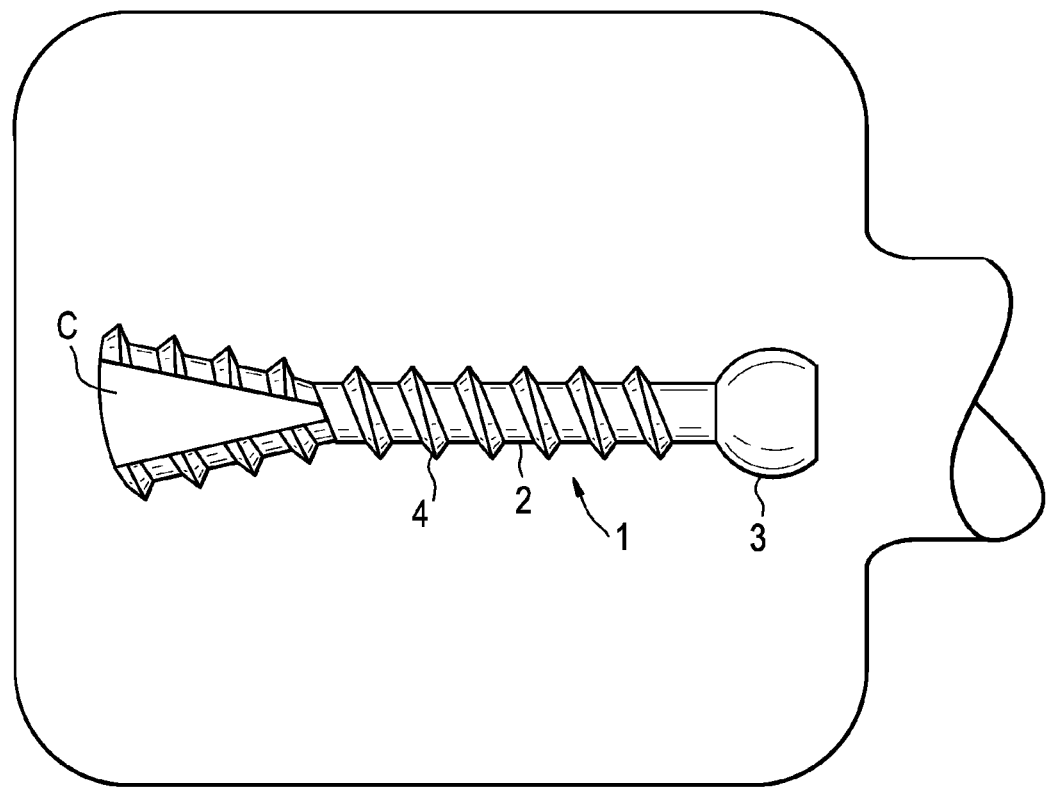
Figure 3D:
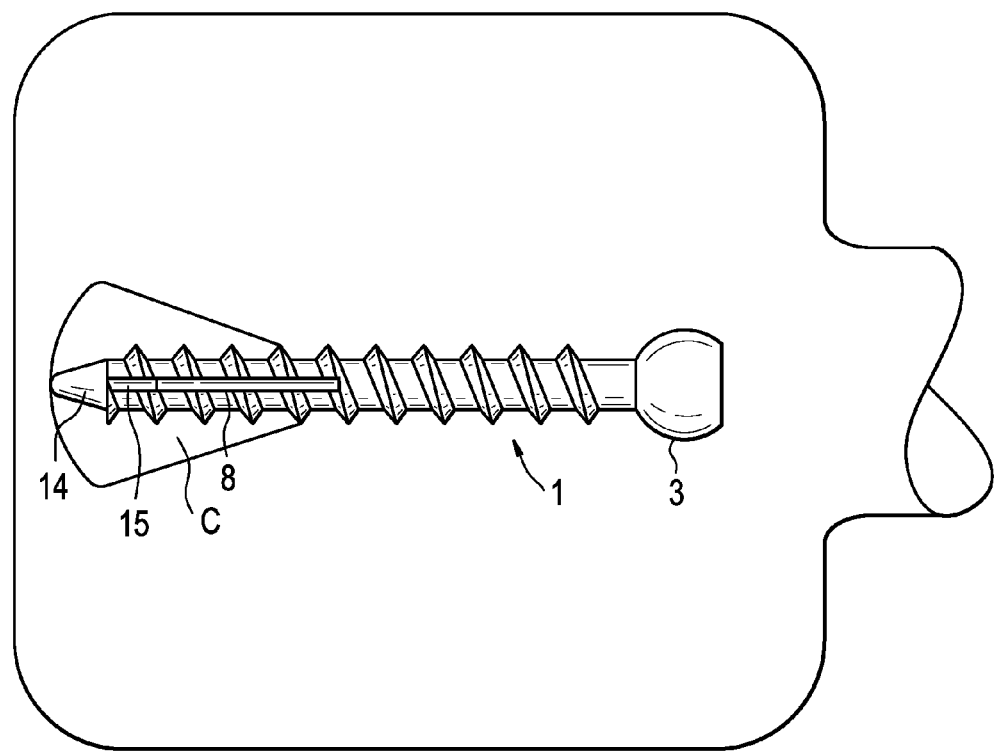
Figure 3E:
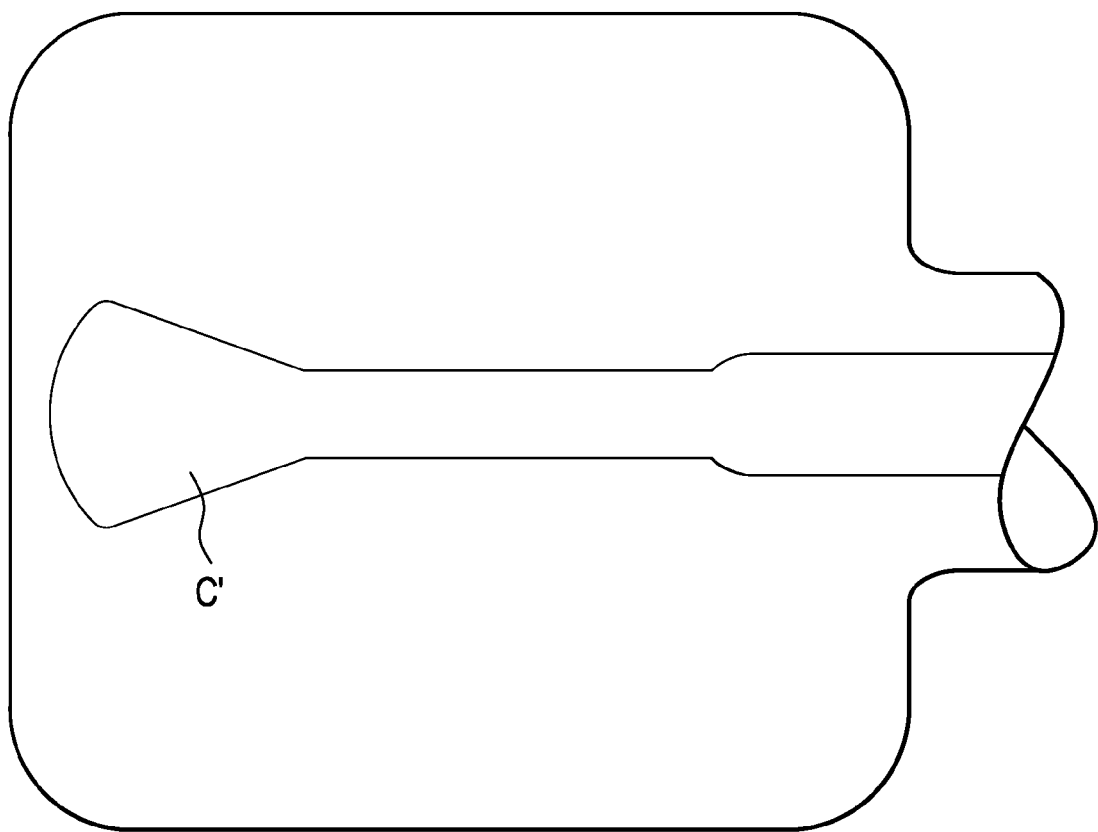
Figure 3F:
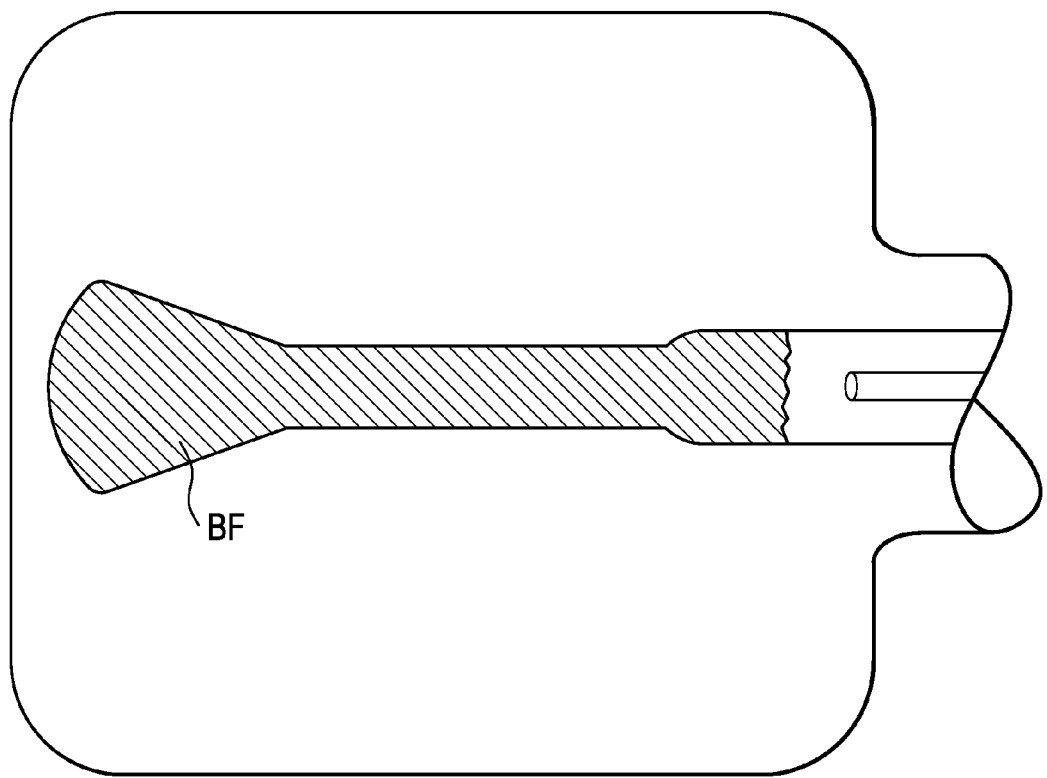

Now referring to FIGS. 3a-3f, there is provided one preferred technique of practicing the present invention. FIG. 3a discloses a defect D in a fractured vertebral body VB. FIG. 3b discloses a bone screw 1 of the present invention inserted into the fractured vertebral body in its collapsed configuration. FIG. 3c discloses expanding the bone screw 1 within the vertebral body to create a cavity C. FIG. 3d discloses re-collapsing the bone screw within the vertebral body. FIG. 3e discloses vertebral body with the bone screw removed, leaving behind cavity C'. FIG. 3f discloses filling the cavity with a bone filler BF.

Other screw-based embodiments are contemplated and include interference screws, suture anchors, stabilizing threads and cemented screw clusters.

Figure 4A:
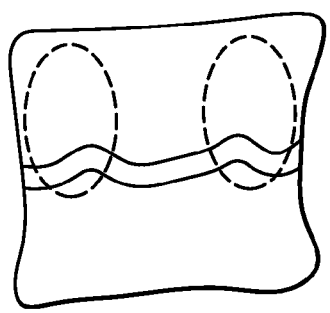
FIGS. 4a and 4b discloses front and side views of a fractured vertebral body.
Figure 4B:
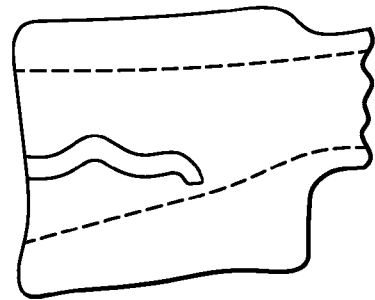
Figure 4C:
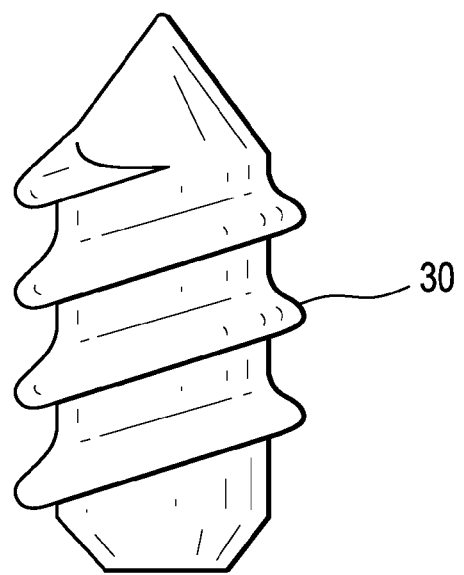
FIG. 4c shows a standard interference screw.
Figure 4D:
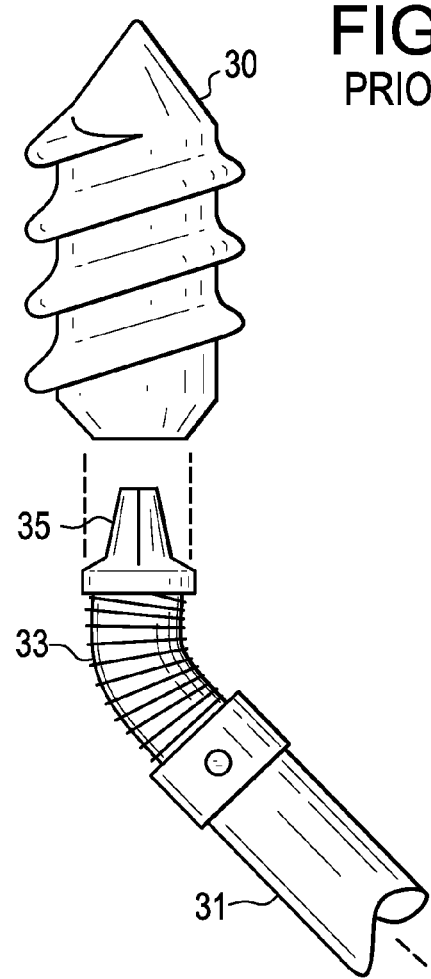
FIG. 4d discloses an exploded view of a standard interference screw-driver assembly.
Figure 4E:
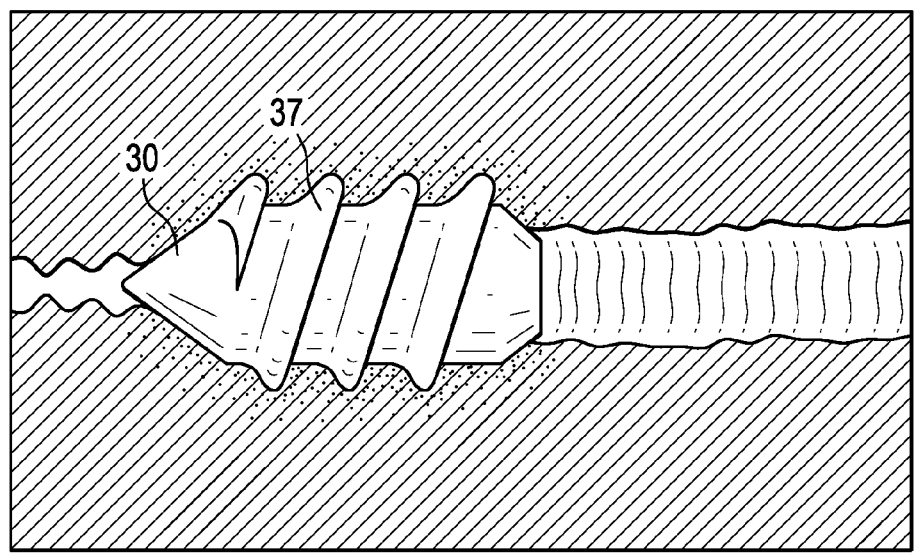
FIG. 4e discloses a side view of an interference screw located at a fracture plane of a fractured vertebral body.

In one interference screw embodiment, the clinician first radiographically views the fracture site, as shown in FIGS. 4a and 4b. Next, the clinician selects a standard interference screw 30, such as the MILAGRO™ screw, marketed by DePuy Mitek of Raynham, Mass., as shown in FIG. 4c. In some embodiments, this screw may be made from materials such as PMMA, high density polyethylene and titanium alloy. The clinician then attaches the proximal end of the screw to a driver such as that shown in FIG. 4d. One representative driver has a proximal straight shaft 31, an intermediate angled shaft 33, and a distal tapered connection feature 35. The distal tapered connection feature forms a mating connection with a tapered recess (not shown) present in the proximal end portion of the interference screw. The clinician then inserts the assembly into a fractured vertebral body and releases the interference screw, so that the interference screw remains in the fracture, as shown in FIG. 4e. The screw displaces bone marrow and compacts the cancellous bone surrounding the screw. The threads 37 of the screw help stabilize the fracture surfaces and may help stabilize the bone fragments.

Figure 5:
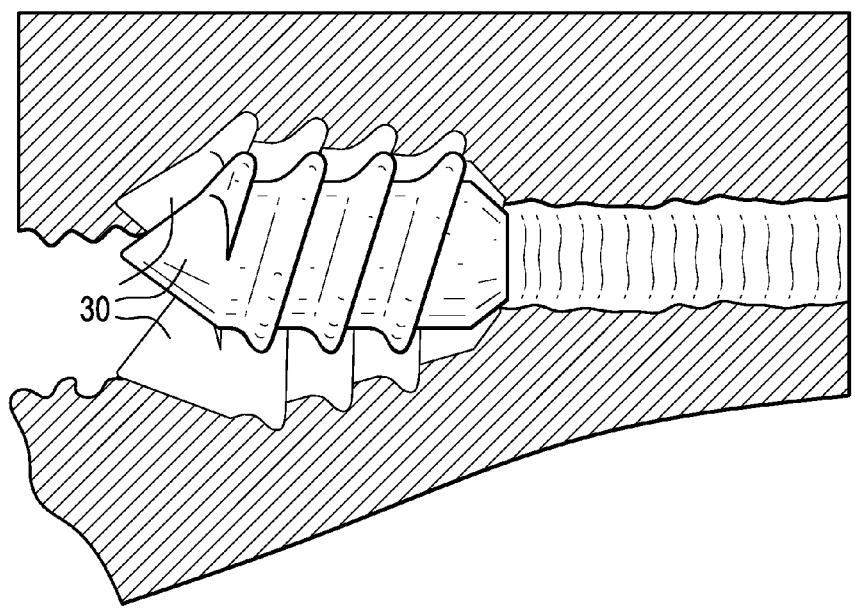
FIG. 5 discloses a pair of interference screw placed adjacent each other and cemented into place in a fractured vertebral body.

In some embodiments thereof, the clinician may choose to insert multiple interference screws 30 into the vertebral body adjacent to one another with varying trajectories, and then inject cement around this cluster of screws. This is shown in FIG. 5

Figure 6A:
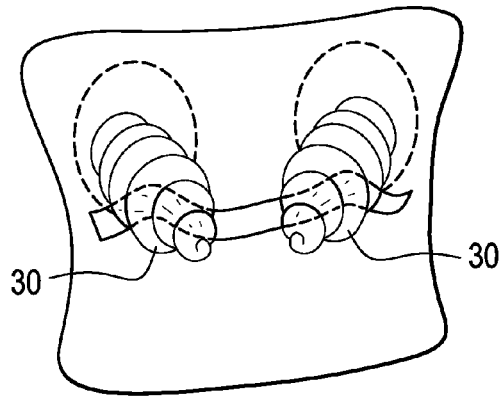
FIGS. 6a and 6b disclose a pair of interference screw placed bipedicularly along a fracture plane in a fractured vertebral body.
Figure 6B:
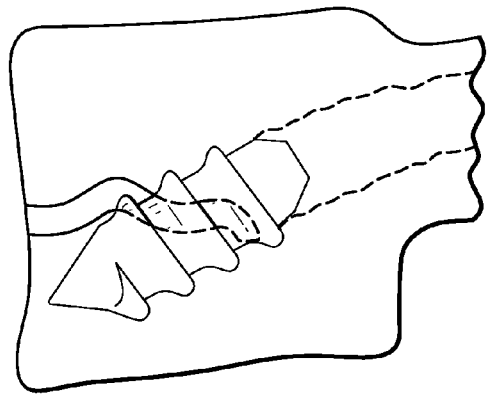

In some embodiments, the interference screws 30 may be placed bipedicularly, as shown in FIGS. 6a and 6b.

Figure 7A:
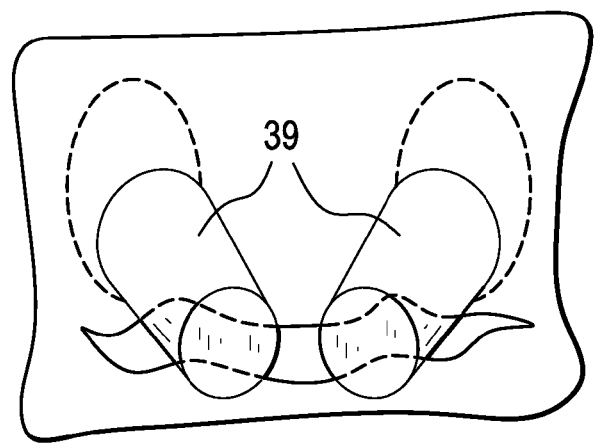
FIGS. 7a and 7b disclose a pair of dowels placed bipedicularly in a vertebral body.
Figure 7B:
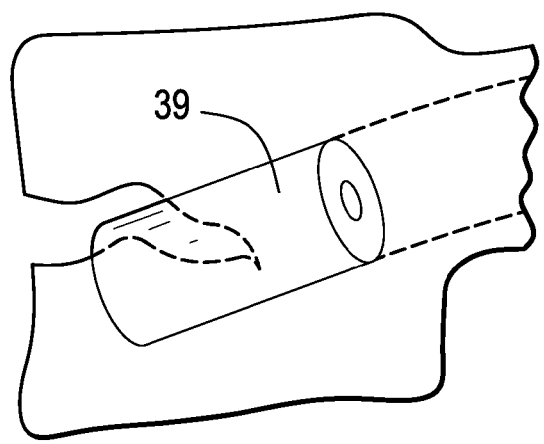

In some embodiments, dowel-shaped sleeves 39 may be placed bipedicularly, as shown in FIGS. 7a and 7b.

Figure 8A:
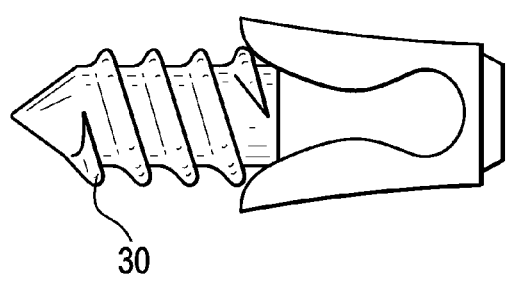
FIGS. 8a and 8b discloses an expandable sleeve in its collapsed and expanded configuration.
Figure 8B:
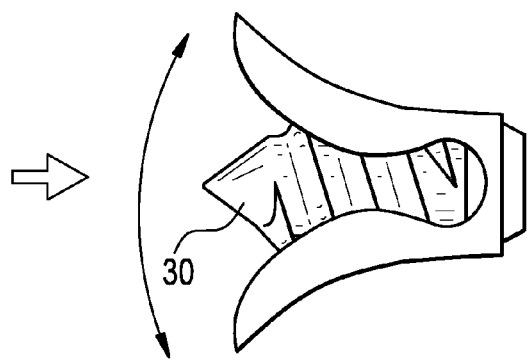
Figure 9A:
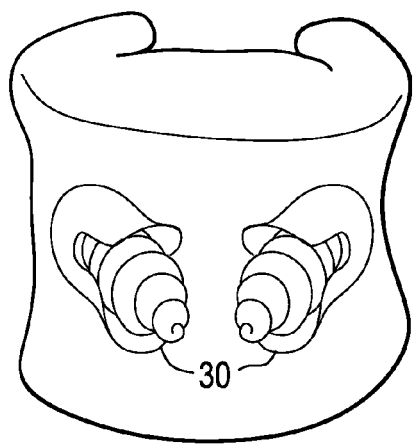
FIGS. 9a and 9b disclose a pair of expanded sleeves placed bipedicularly in a vertebral body.
Figure 9B:
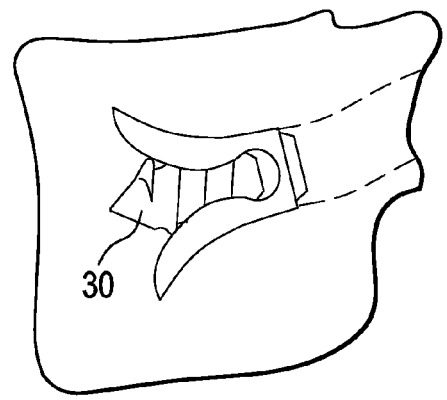

In some embodiments, the interference screw 30 can be used as the mandrel of the expandable sleeve embodiments discussed above, as shown in FIGS. 8a and 8b. This assembly can be used bipedicularly, as shown in FIGS. 9a and 9b.

Therefore, in accordance with the present invention, there is provided a method of augmenting a fractured vertebral body, comprising the steps of:
a) inserting a first interference screw into the vertebral body,
b) inserting a second interference screw into the vertebral body adjacent the first interference screw, and
c) contacting each of the inserted screws with bone cement.

Figure 10A:
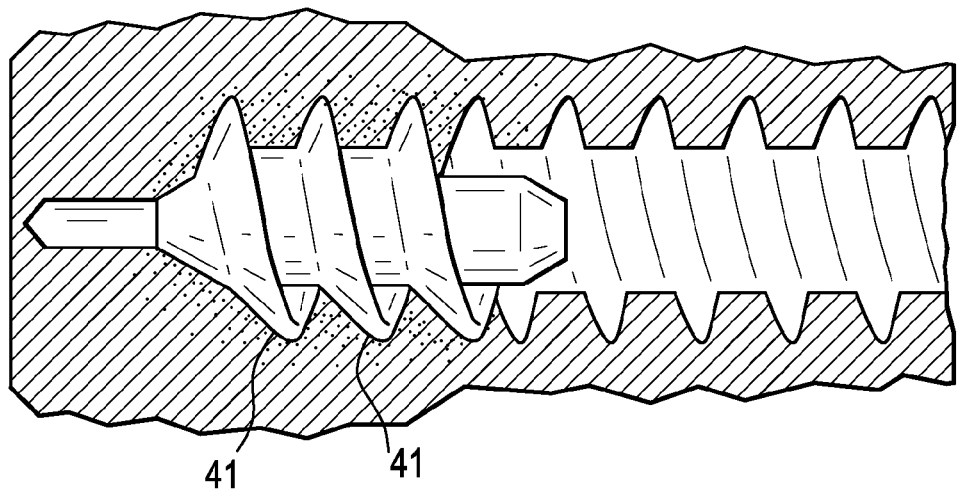
FIGS. 10a and 10b disclose interference screws with large and small threads.
Figure 10B:
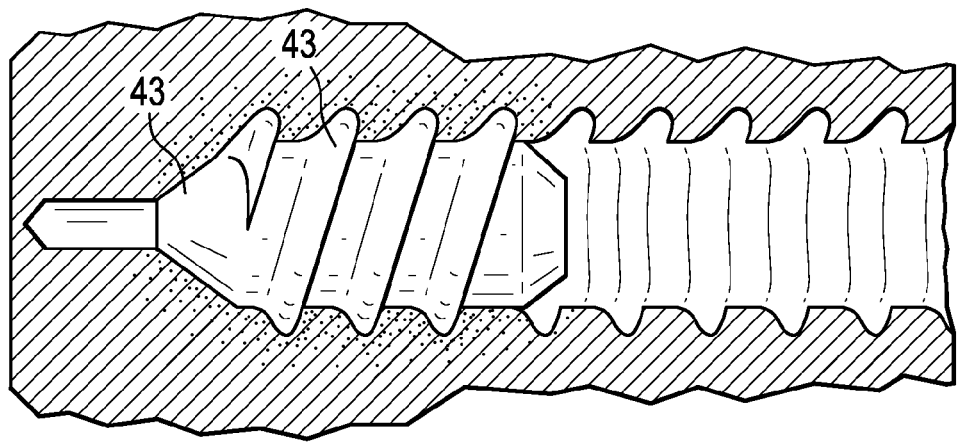

The screw threads can be designed to maximize bone fragment stabilization during fracture reduction, or they can be optimized to enable expanded screw rotation. Screw threads also enable controlled screw insertion. Deep threads (deeper thread height) can be selected to stabilize bone fragments during shank deflection. However, deep threads might frustrate deflected screw rotation, so shallow threads may be the preferred embodiment for a method that includes rotation of a deflected screw. A deep thread 41 is shown in FIG. 10a, and a shallow thread 43 is shown in FIG. 10b.

It may be preferable to have a portion of the screw threads rotate independently of the screw shaft (e.g., a threaded barrel around a portion of the screw). Such a mechanism would enable rotation of the deflected screw without axial motion (because the threaded barrel would not rotate while the screw was rotated to accomplish bone tamping).

In many embodiments, the device has a standard mandrel having a proximal side having a circumferentially uniform taper, as in FIG. 1.

It may be further possible to off-set the mandrel to force screw shaft deflections in preferential directions (i.e. the screw shaft material deflects more to one side than the other). This can be accomplished by designing the mechanical compliance of at least one leg of the shaft to be more easily deflected by mandrel loading. Alternatively, geometric designs of the cannulation or mandrel could cause preferential shaft deflection (such as a ramp or tooth, a divot, thinning or thickening the wall). Hardinge contemplates multiple ramps. Serial nesting of these ramps can provide significant deflection of the screw walls or more precise control of wall deflection at various points along the screw shaft.

Figure 11:
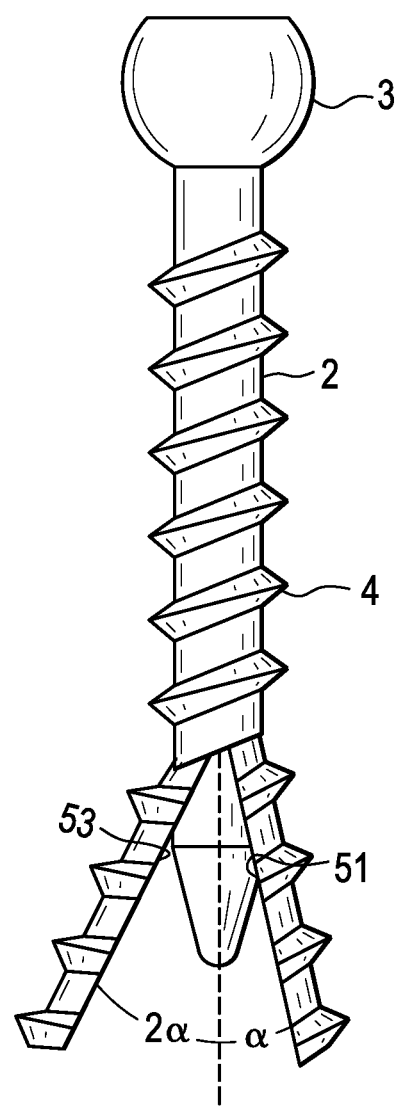
FIG. 11 discloses a bone screw of the present invention in a vertebral body in its expanded configuration, with its legs splayed at different angles.

In one such off-set embodiment, and now referring to FIG. 11, the mandrel 50 has a first proximal side 51 having a first taper angle and a second proximal side 53 having a second larger taper angle. When this mandrel is moved proximally (without rotation) to contact the shaft, the difference in taper angle produces shaft legs that are splayed from the shaft proper at different angles. When this expanded screw is then rotated, these legs tamp different conical portions of the surrounding bone, thereby forming a cavity that is larger than the cavity produced by legs splayed at the same angle.

Figure 12:
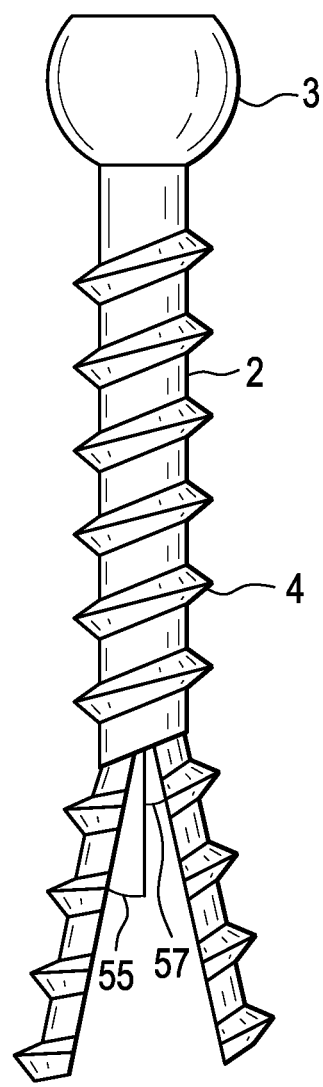
FIGS. 12-14 disclose various screws adapted to provide legs splayed at different angles.

Now referring to FIG. 12, in another embodiment, the mandrel may be a split mandrel. In this embodiment, the mandrel comprises mandrel-halves 55,57 that are capable of independent axial sliding movement. When the mandrel halves are moved proximally into the shaft to different levels of penetration, each leg splays in an amount that depends upon the level of penetration of its corresponding mandrel-half. That is, the mandrel half 57 that has a relatively deep penetration produces a leg with a large angle splay, and the mandrel half 55 that has a relatively shallow penetration produces a leg with a small angle splay. When this expanded screw is then rotated, these legs tamp different conical portions of the surrounding bone, thereby forming a cavity that is larger than the cavity produced by legs splayed at the same angle.

Figure 13:
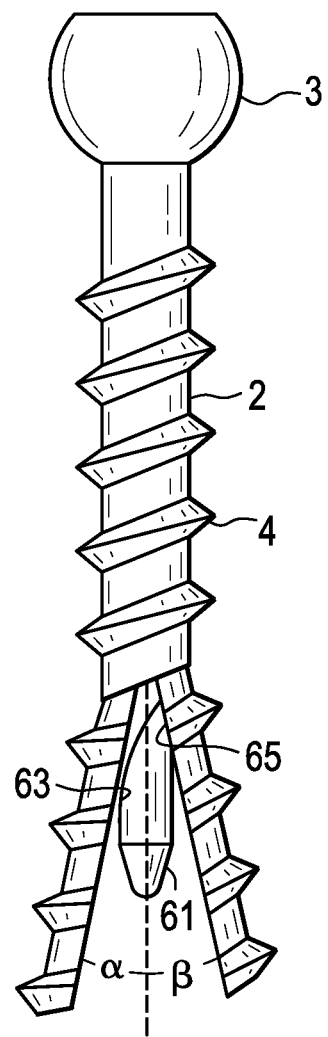

Now referring to FIG. 13, in another embodiment, the mandrel 61 has staggered tapers. In particular, the mandrel has a first proximal side 63 having a first taper that extends proximally a first distance and a second proximal side 65 having a second taper that extends proximally a second longer distance. As this mandrel moves proximally to contact the shaft, the second taper extends deeper into the shaft and thus splays the associated leg to a greater angle.

In another embodiment, the standard mandrel is first inserted into the shaft bore a first distance so that the legs splay at a first angle. The device is then rotated so that bone in a first conical region is tamped. Next, the mandrel is inserted deeper into the bore so that the legs become splayed at a second larger angle. The device is again rotated so that bone in a second, more shallow conical region is tamped. This process may be repeated at increasingly larger splay angles in order to achieve increasingly larger cavity volumes.

Figure 14:
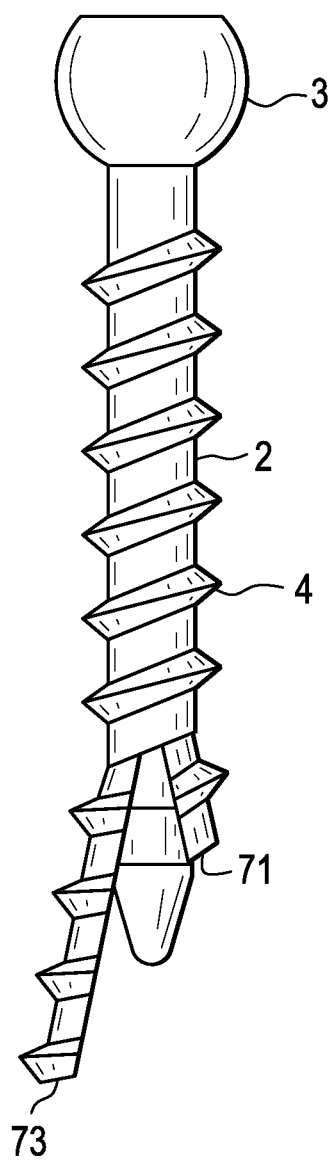

Now referring to FIG. 14, in another embodiment, the first leg 71 of the shaft extends a first distance and the second leg 73 of the shaft extends a second longer distance. When the standard mandrel is moved proximally into the shaft, the mandrel first begins to splay the longer shaft leg. The shaft may then be rotated. Proceeding further proximally, the mandrel further splays the longer shaft leg while beginning to splay the shorter shaft leg. The shaft may then be rotated. This process may be repeated at increasingly larger splay angles in order to achieve increasingly larger cavity volumes.

In another embodiment, a plurality of expandable screws of the present invention are delivered in a side-by-side manner in a manner similar to the side-by-side delivery of interference (nonexpanding) screws shown in FIG. 5.

Figure 15A:
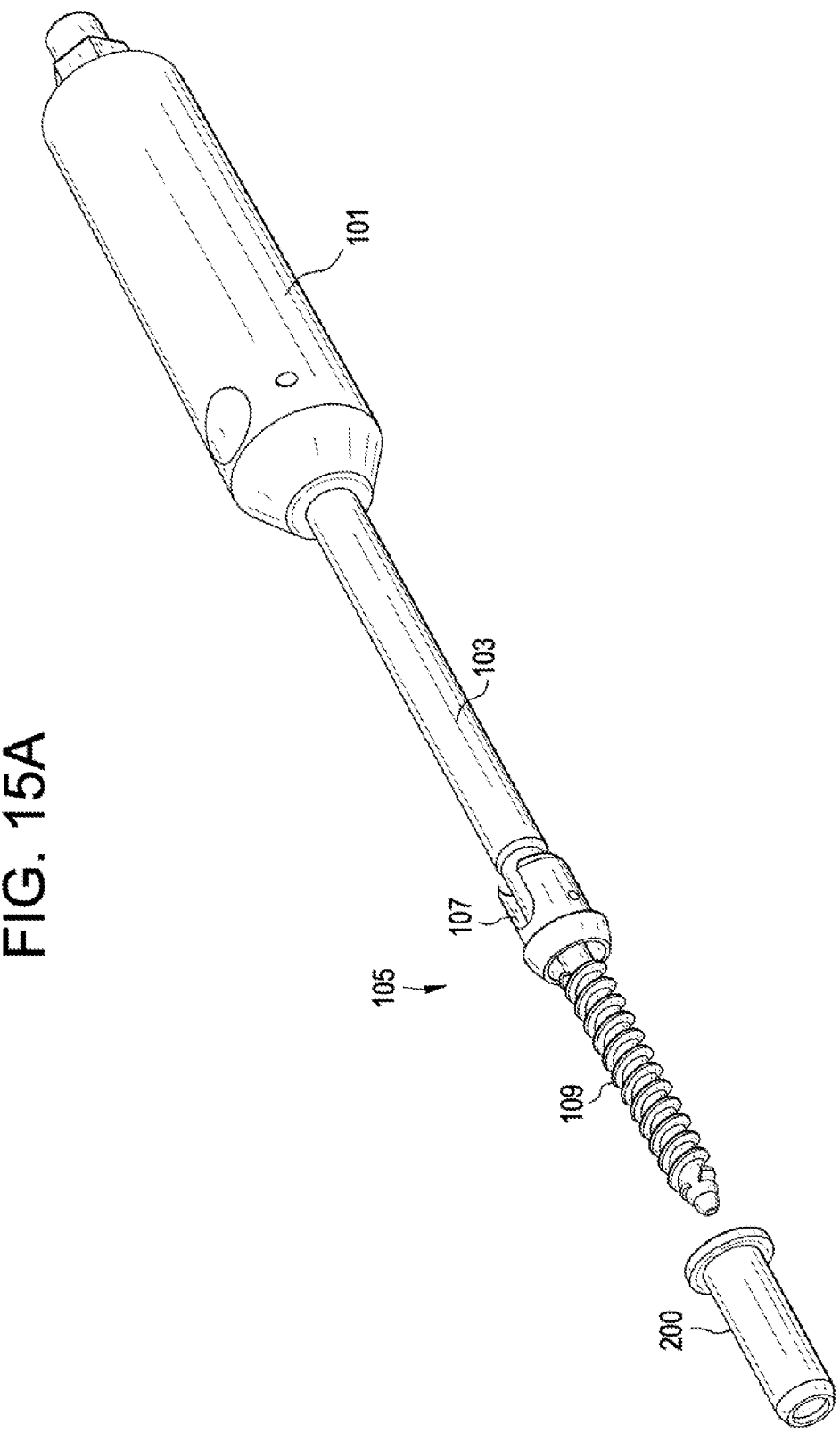

In another embodiment, and now referring to FIGS. 15a-15c, there is provided an instrument for creating a space in a vertebral body. The instrument comprises a proximal cannulated handle 101 having a throughbore, a barrel 103 extending from the distal portion of the handle, and a distal screw 105 extending from the barrel, wherein the screw comprises a head 107 and a cannulated threaded split shaft 109. Extending through the cannulae of the respective components is a cannulated split tip rod 111 and a central engagement rod 113. The split tip rod 111 has a hex bolt on its proximal end. Near the distal end of the device is a retractable anvil 115. This device operates along the same general principles discussed above for the instrument of FIGS. 1a-2. In particular, the split tip rod is retracted and the retracting anvil opens the threaded shaft. If desired, the engagement rod 113 can be removed and cement may be delivered through the resulting bore.

We claim:

1. A method of augmenting a fractured vertebral body in a patient, comprising the steps of:
    a) selecting an expandable sleeve characterized by a collapsed configuration and an expanded configuration, and comprising a cannulated shaft having a bore, a proximal end, a distal end, a threaded bushing and a plurality of longitudinal slits opening onto the distal end and forming at least two legs in the cannulated shaft,
    b) inserting the expandable sleeve into the fractured vertebral body in its collapsed configuration,
    c) expanding the sleeve to its expanded configuration to tamp the fractured vertebral body,
    d) rotating the expanded sleeve without simultaneous longitudinal movement of the rotating expanded sleeve so that bone in a first conical region is tamped,
    e) returning the expanded sleeve to its collapsed configuration,
    f) removing the sleeve from the vertebral body to leave a cavity having a conical region in the fractured vertebral body, and
    g) filling the cavity with bone cement.

2. The method of claim 1 wherein the expandable sleeve is a bone screw comprising a cannulated, threaded shaft.

3. The method of claim 2 wherein the expandable bone screw further comprises a mandrel having a distal end portion having a diameter larger than the bore, wherein the expanding step comprises moving the mandrel proximally within the threaded, cannulated shaft.

4. The method of claim 3 wherein the distal end portion of the mandrel comprises a tapered proximal portion.

5. The method of claim 3 wherein the mandrel has an asymmetric radial geometry that causes preferential leg deflection.

6. The method of claim 2 wherein a first leg has an elasticity, a second leg has an elasticity, and the elasticity of the first leg is greater than the elasticity of the second leg.

7. The method of claim 2 wherein the cannulated, threaded shaft comprises a plurality of deep threads.

8. The method of claim 2 wherein the cannulated, threaded shaft comprises a plurality of shallow threads.

9. The method of claim 2 further comprising the step of rotating the expanded screw in the fractured vertebral body.

10. The method of claim 9 wherein the rotation causes distal movement of the expanded screw.

* * * * *